United States Patent
Chung et al.

(12)

(10) Patent No.: US 6,265,217 B1
(45) Date of Patent: Jul. 24, 2001

(54) METHOD FOR PRODUCING MICROBULBS OF GARLIC {ALLIUM SATIVUM L.} IN VITRO

(75) Inventors: Kyung Ho Chung, Kyonggi-Do; Sang Il Nam, Seoul, both of (KR)

(73) Assignee: Tong Yang Moolsan Company Limited (KR)

( * ) Notice: Subject to any disclaimer, the term of this patent is extended or adjusted under 35 U.S.C. 154(b) by 0 days.

(21) Appl. No.: 09/516,070

(22) Filed: Mar. 1, 2000

(51) Int. Cl.$^7$ ...................................................... C12N 5/00
(52) U.S. Cl. .......................... 435/420; 435/410; 435/430; 435/430.1; 435/431; 47/58.1
(58) Field of Search ...................................... 435/410, 420, 435/430, 430.1, 431; 47/58.1

(56) References Cited

U.S. PATENT DOCUMENTS

| | | | |
|---|---|---|---|
| 5,413,929 | * | 5/1995 | Ishizaki et al. . |
| 5,587,312 | * | 12/1996 | Van Holst et al. . |
| 5,746,024 | * | 5/1998 | Rice et al. . |

OTHER PUBLICATIONS

Yasseen Mohamed–Yassen, Sheryl A. Barringer, and Walter E. Spittstoesser. 1995. In vitro bulb production from Allium spp. In vitro cellular and developmental biology–plant 31(1):51–52.

J. A. Romberger and C. A. Tabor (1971) "The *Picea*Abies Shoot Apical Meristem In Culture. I. Agar and Autoclaving Effects".

Sara Von Arnold and Tage Eriksson (1979) "Induction of Adventitious Buds on Buds of Norway Spruce (*Picea abies*) Grown in vitro".

M. Faye, A. David, and A. Lamant (1986) "Nitrate reductase activity and nitrate accumulation in in vitro produced axially shoots, plantlets and seedlings of *Pinus pinaster* ".

P. Debergh, Y. Harbaoui and R. Lemeur (1981) "Mass propagation of globe artichoke (*Cynara scolymus* ): Evaluation of different hypotheses to overcome vitrification with special reference to water potential".

Wernicke and Kohlenbach Investigations on Liquid Culture Medium as a Means of Anther Culture in Nicotiana (1976).

* cited by examiner

*Primary Examiner*—Leon B. Lankford, Jr.
(74) *Attorney, Agent, or Firm*—Akerman Senterfitt

(57) ABSTRACT

A method for producing the bulbs of Garlic with saving the cost for producing them and enhancing the work efficiency and the yield by dark-culturing and/or liquid media-culturing of the garlic tissues in vitro is provided, which comprises the steps of:

a) isolation and excision of the virus-free tissues in the length of 0.2 to 0.3 mm obtained from the meristem of parent body of garlic;

b) inoculating the excised tissues from the meristem tissue of garlic onto the solid-type primary media;

c) culturing the tissues inoculated onto the solid-type primary media under the light condition at 25° C. in the culturing room for 4 weeks;

d) propagating the shoots regenerated from the cultured tissues at the multiplication media for 4 weeks;

e) transferring the propagated shoots into the liquid-type media with additional components of 90 g/l of sucrose and plant growth regulators and culturing them primarily for 10 days;

f) transferring the primarily cultured tissues into the liquid-type media having the same composition as the media used in the step e) with additional components of 140 g/l of sucrose and plant growth regulators;

g) secondarily culturing the said tissues at about 25° C. and under the dark-condition in the culturing room for 6 weeks;

h) harvesting the microbulbs from the virus-free garlic plants in vitro;

in which the steps f) and g) are carried out in the altered liquid-type MS media under the dark-condition with no artificial illumination.

11 Claims, No Drawings

METHOD FOR PRODUCING MICROBULBS OF GARLIC {ALLIUM SATIVUM L.} IN VITRO

BACKGROUND

1. Field of the Invention

The present invention relates to a method for producing the bulbs of Garlic In Vitro, more practically, a method for producing the bulbs of Garlic with saving the cost for producing them and enhancing the work efficiency and the yield by dark-culturing and/or liquid media-culturing of the tissue of garlic In Vitro.

2. Description of the Related Art

Generally, the garlic is known to be propagated by vegetative propagation through dividing the clove, since their reproductive organ had been degenerated and no seeds are formed in the plant body itself. In addition, since the ratio of obtaining the clove is very low, much more amount of clove should be used as the "seeds" in cultivation of the garlic.

Furthermore, the garlic is generally exposed to a risk of possible infection of the virus, and once a parent body of the garlic is infected by the virus, the progenies resulted from the said parent body by the vegetative propagation are grown in the infected condition thereby causing the reduced yield of garlic.

In order to produce the virus-free garlic, it has been believed as the possible way, to isolate and excise the meristem tissues from the garlic, which is the sole virus-free tissue in the plant, so that the seed garlic may be produced by propagation through the tissue culture technique. However, since there consumed the significant amount of costs in producing the virus free seed garlic in the industrial scale for the practical agriculture of the farmers, such processes could not have been carried out.

For instance, the maintenance costs of tissue-culturing room for producing the seed garlic in the industrial scale according to the conventional manner comprise, generally, about 40% of labour cost, about 10% of cost for preparing the culture media, about 50% of cost for maintenance and management of the equipments and the work costs. From the above-mentioned costs, the latest costs which correspond to the largest portion is consumed for illuminating and air-conditioning of the room, heating of media according to the process and/or disposal of the waste media.

The efficiency of the basic costs for tissue-culturing depends on the rate of propagation and the amount of production of garlic microbulbs to be implanted in the ground. Therefore, the various methods for increasing the propagation efficiency have been studied, including the propagation of callus of garlic, the propagation of tissue-cultured shoot primordia, and the propagation of the shoots. However, as a result of studying the experiments and tests reported up to now, the present inventors found that the method for propagation of the garlic by tissue culture technique is the most advantageous way for increasing the yield of microbulbs.

For instance, the conventional methods for producing the virus-free body by the tissue-culturing process of garlic, in general, are carried out by the following steps:

a) isolation and excision of the meristem tissue as the virus free tissue from the parent plant body of garlic;

b) culturing the said tissue obtained from the meristem and propagation of the shoots from the said cultured tissue; and c) forming the small microbulbs in vitro from the said propagated shoots.

According to the above-mentioned method, it is found that the most important factors for effecting the yield of production are to providing with a suitable conditions of the environment and media for culturing, propagation and growth of the tissue in the steps of b) and c). In other words, if for the same period, the same amounts of virus-free microbulbs are produced in the suitable media and environmental condition, the main factors for the cost are the expenses of preparing the culture media, culturing equipment, and the cost for managing the electric equipments to keep the various conditions in the culturing room.

In this regard, the material costs for producing the microbulbs and the maintenances thereof mainly consist of the costs for preparing the media and keeping the illumination and electric supply and the cost for maintaining the equipment.

Conventionally, the solid type media has been used as the said media. Among the said costs, the expense for preparing the gelling agent has the main portion of the costs. Especially, the agarose media is thought as being the most preferable gelling agent. However, the price of the said agarose media as gelling agent is high, and furthermore, since the agarose is thermo-sensitive, it may be solidified only under a predetermined temperature.

Accordingly, due to the high price of the agar, much amount of expense are needed for preparing the solid type media, and since the media should be heated to above the predetermined temperature and re-solidified after carrying out the required work during the liquid state (the work should be carried only in the liquid state), the ease and efficiency of work is not satisfactory, and there also exist the problems in the processes and expenses.

As mentioned, the reason for the gelling agents such as agarose to be used in spite of the various problems, is to prevent the plants to be cultured from exhibiting the phenomena of vitrification or caulogenesis. It is found that the agar has some constituents to inhibit such phenomena (Romberger and Tabor (1971), Wernicke and Kohlenbach (1976)).

The concentration of agarose in the media has been confirmed in many studies and reports, as being directly related to the growth of plants. Especially, semi-fluid media is believed to be relatively advantageous to be used in the step before being implanted in the soil (ground), because relative to the solid media, the nutrients readily flow in the liquid media and enhance the growth of in vitro plants, and the liquid media may be easily removed from the plant body (Von Arnold and Eriksson, 1979).

Also, Faye et al. (1986) recently reported that the shoots and the plantlets grown in the liquid media are superior to those of grown in the agarose media in an aspect of uptaking the nitrogen constituents from the media.

Furthermore, Romberger and Tabor (1971) reported that the flow of large molecules is restricted in agarose media, and the growth of plants is adversely effected by the immobilization of invertase released from the culturing plants.

Debergh et al. (1981) also reported that since the micro elements and the phosphate constituents are absorbed by the agarose matrix itself, the amounts absorbed by the culturing plants are significantly reduced. Furthermore, they also reported that the absorption of the growth regulator, the mineral ions and the organic substances are restricted as the same way (Debergh, 1982). Therefore, it is believed that the agarose has the advantageous effects and functions as the media, it also has the adverse effects to restrict the growth and development of the in vitro plant.

Also, the prior liquid-type media has a problem that the rate of vitrified tissues is increased so it has not put to practical use.

For these reasons, the present inventors have researched and developed a novel and more effective media for using in culturing the tissue of garlic.

In other aspect, it was essentially known to the ordinary person skilled in the field of art that such as about 5,000 lux of illumination should be provided with the tissues cultured in the conventional solid type media for producing the microbulbs. For such illumination, throughout the period over about 6 weeks, the significant amount of the electric power should continuously be provided with the equipments in the room. For this purpose, various and many equipments for illumination should be provided in the room. Furthermore, since the additional equipments for air conditioning in the culturing room should be installed and continuously operated in order to control the room temperature within the optimum condition, which is successively raised by the illumination equipments, etc., it cannot be avoided to increase the production cost in case of the industrial scale.

As a matter of fact, since it has been believed that the illumination of the lights is essential for tissue culture of garlic, no case to approach the removal of illumination during the culturing period (that is, dark culture) has been reported in spite of such large amount of costs.

SUMMARY OF THE INVENTION

In order to solve the afore-mentioned problems according to the conventional processes, an object of the present invention is to provide a method for producing the microbulbs of Garlic with significantly saving the costs for producing them on one hand, as well as enhancing the work efficiency and the yield over than approached by the prior arts, on the other hand, by dark-culturing and/or liquid media-culturing of the tissue of garlic, in vitro.

The other objection of the present invention is to provide a novel liquid-type media for using in the method according to the first objection as mentioned above.

As a result of carrying out the intensive and extensive experiments for culture by using the various conditions of the media and/or the artificial illumination in order to achieve the objects of the present invention, the present inventors found that a significantly improved culturing efficiency over the prior art may be achieved by using the liquid-type media and the dark-condition (with providing with substantially no artificial illumination), and completed the present invention.

According to an aspect of the present invention, an improved method is provided in which a significantly improved culturing efficiency over the prior art may be achieved by using the liquid-type media instead of the solid-type media used in the prior art and simultaneously with using the dark-condition without providing any artificial illumination, so that the cost for production including the expenses for installation and management of the equipments is reduced, and the problems of the work efficiency and the disposal of waste are improved.

In a preferred embodiment, the method according to the present invention comprises the following steps:

a) isolation and excision of the virus-free tissues in the length of 0.2 to 0.3 mm obtained from the meristem tissue of parent body of garlic;

b) inoculating the selected and collected tissues from the meristem tissue of garlic onto the solid-type media;

c) culturing the tissues inoculated onto the solid-type media under the light condition at 25° C. in the culturing room for 4 weeks;

d) propagating the shoots regenerated from the cultured tissues at the propagating media for 4 weeks;

e) transferring the propagated shoots into the liquid-type media with additional components of 90 g/l of sucrose and plant growth regulators and culturing them primarily for 10 days;

f) transferring the primarily cultured tissues into the liquid-type media having the same composition as the media used in the step e) with additional components of 140 g/l of sucrose and plant growth regulators;

g) secondarily culturing the said tissues at about 25° C. and under the dark-condition in the culturing room for 6 weeks;

h) harvesting the microbulbs from the virus-free garlic plants in vitro in which the steps f) and g) are carried out in the altered liquid-type MS basal media under the dark-condition with no artificial illumination.

The media preferably used in the present invention is prepared based on the conventional MS media according to the prior art, which has been used in the various experiments for culturing most of plants and microorganisms. The essential composition of the MS media which may be used in the invention is provided in the Table 1 as below:

TABLE 1

| Composition of MS Media* | |
|---|---|
| Component | Conc. in Media (mg/l) |
| STOCK A-1 | |
| $NH_4NO_3$ | 1650 |
| $KNO_3$ | 1900 |
| $MgSO_4.7H_2O$ | 370 |
| $KH_2PO_4$ | 170 |
| STOCK A-2 | |
| $CaCl_2$ | 440 |
| STOCK B | |
| KI | 0.83 |
| $H_3BO_3$ | 6.2 |
| $MnSO_4$ | 15.1 |
| $ZnSO_4.7H_2O$ | 8.6 |
| $NaZMoO_4.2H_2O$ | 0.25 |
| $CuSO_4.5H_2O$ | 0.025 |
| $CoCl.6H_2O$ | 0.025 |
| STOCK C | |
| FeNaEDTA | 3.671 |
| VITAMINS | |
| myo-inositol | 100 |
| nicotinic acid | 0.5 |
| pyridoxine-HCl | 0.5 |
| thiamin-HCl | 0.5 |
| glycine | 2 |
| pH = 5.8 | |

The modified liquid media used in the method of the present invention was prepared by altering the concentration of $NH_4NO_3$ on the basis of the composition of the MS media provided in Table 1. The more detailed explanation will be given hereinafter.

Alternately, the tissues used in the step c) are obtained from an axillary bud grown in the artificial media within two (2) months.

DETAILED DESCRIPTION OF THE PREFERRED EMBODIMENT

EXAMPLES

Hereinafter, the present invention is described by the specific examples in detail, however, the scope of the invention should not be understood to be limited only to the examples.

Experiment:

In vitro shoots of the garlic to be used in the method of the invention are made according to the following processes:

1. Preparation of the Material for Experiment Plant:

1) The plant bodies of garlic, which were implanted into the ground around the end of October, in autumn, and grown from the next spring to be two (2) weeks aged from starting the splitting, were wholly obtained with their roots and transported to the laboratory.

2) The leaves of uppermost part of garlic body which are budding out of the roots was removed in the clean bench, and they were sterilized in 70% ethyl alcohol for 1 minute and then in 4% sodium hypochrolite solution for 10 minutes. Thereafter, they were washed three times with sterilized distilled water, and the meristem tissues were isolated and excised under microscopic observation.

3) The tissues of the size of up to 0.2 mm from were chosen from the meristem tissue, and implanted onto the artificial media in the solid type. For this process, the shoots induced directly from the meristem tissues may be used, however, the multishoots propagated in the artificial media for the multiplication of shoot are preferable.

Media:

1) MS basal media containing 0.2 mg/l of Cytokinin (BA) was used as the media for inoculation of the meristem tissues.

2) 2.0 mg/l conc. of Cytokinin (BA) as the plant growth regulator was added to the MS basal media for shoot proliferation.

3) 20 g/l of sucrose as the carbon source and 6.5 g/l of agar as the gelling agent were added to the media for producing the samples.

4) The media was autoclaved in the state of 1.2 kg/cm$^2$ for 15 minutes, and then separated into each petridish (100 mm diameter×16 mm height) for producing the samples.

Period:

Each period of experimental culture was for 4 weeks.

Condition of the Culturing Room:

The temperature in the culturing room was kept 25±1° C., and the light source (fluorescent lamp) of 5000 lux was used for 16 h (light condition)/8 h (dark condition).

2. Forming the Microbulbs in the Liquid-Type Media
Experiment 1. Micro Bulbs-Forming Percentage and Vitrification Percentage According to the Agar Concentration In order to search what an effect in aspect of 1) microbulb-forming percentage; 2) productivity of microbulb; and 3) causing the vitrification of plant body, may be resulted from the concentration of agar in the media during the stage of forming the bulbs, a series of test was carried out for determining the microbulb-forming percentage, the amount of the produced microbulbs; and the percentage of the vitrification caused in the plant body, by using six (6) kinds of media with the various concentrations of agar, including the liquid type media with no agar constituent.

Example 1

The media used in the experiment was prepared by adding 90 g/l of sucrose to the MS media. On the condition of adding agar to each of liquid-type media in the concentrations of 0, 3, 6, 9, 12 and 15 g/l, pH was adjusted to about 5.8 by using 1N NaOH and 1N HCl solutions, the agar was added and dissolved by boiling the mixed media in the microwave oven. The agar-added media was divided by each volume of 80 ml and introduced into the round shape of polypropylene vessels (diameter of 110 mm×height of 45 mm) and autoclaved at 120° C. for 15 minutes. After cooling the media to the ambient temperature, 100 samples of plant bodies (garlic) were implanted per vessel. After developing the bulbs for 6 weeks in the culturing room, each determination of 1) microbulb-forming percentage, 2) the productivity of microbulb, and 3) causing the vitrification of plant body was carried out.

The condition of the culturing room was controlled for the temperature of 25±1° C., and about 5000 lux of illumination by using the fluorescent lamps for alternatively 16/8 hours (light/dark it condition). 50 vessels were treated per one process, and the same experiments were repeated three times for calculating the average values of the data. The results are shown in Table 2 as below.

TABLE 2

Forming percentage and produced amount of the garlic microbulbs, and the percentage of vitrification, according to the concentration of agar in media

| Conc. of Agar (g/l) | Micro bulb forming percentage (number of formed bulbs/number of plants × 100) (%) | fresh weight of micro bulbs produced per bottle (g/Bottle) | vitrification percentage (nos. of vitrification cases/ plants × 100) (%) |
|---|---|---|---|
| 0 | 74.3 | 28.3 | 18.4 |
| 3 | 75.1 | 27.7 | 15.6 |
| 6 | 77.1 | 24.7 | 12.4 |
| 9 | 76.5 | 16.6 | 8.3 |
| 12 | 83.4 | 9.4 | 4.2 |
| 15 | 80.0 | 6.2 | 1.7 |

As seen from the result of experiment 1, from the media containing the regular concentration of agar (6 g/l), about 12% of vitrification was observed, while about 21% of vitrification was observed from the liquid media (0% of agar). Contrarily, the fresh weight of microbulbs produced in the liquid media was higher than those from the solid media. Furthermore, it was also observed that the more amount of agar than the regular concentration was added, the better forming percentage of bulbs and the lower percentage of vitrification were achieved. However, the significantly reduced productivity was also observed. Especially, for example, the productivity in the group of media containing 15 g/l of agar was determined as being below ¼ of liquid media having no agar constituent.

From these results, it is deduced that the aforementioned adverse effect of gelling agent also appear in the case of the garlic. On the basis of such results, it is proved that the availability of the liquid media in culturing the garlic is verified in the consideration of an adverse effect of the gelling agent.

Example 2

The liquid-type media used in the experiment was prepared by adding not agar but 90 g/l of sucrose to the MS media. pH was adjusted to about 5.8 by using 1N NaOH and 1N HCl solutions. The media was divided by each volume of 80 ml and introduced into the round shape of polypropylene vessels (diameter of 110 mm×height of 45 mm) and autoclaved at 120° C. for 15 minutes. After cooling the media to the ambient temperature, 100 samples of in vitro shoots were implanted per vessel. After developing the micro bulbs for 6 weeks in the culturing room, each determination of 1) microbulb-forming percentage, 2) the productivity of microbulb, and 3) causing the vitrification of plant body was carried out.

The condition of the culturing room was controlled for the temperature of 25±1° C. The illumination treating experiment was carried out as follows; One condition is a dark condition that is treated for 24 hours without the light from outside and another conditions are light condition that the about 200 to 10,000 lux of illumination is provided. The light condition experiment was carried out in the growth chamber that the desired illumination is provided by using the fluorescent lamps. The lighting hour was adopted from the common tissue culture laboratory that is alternatively 16/8 hours (light/dark condition). 50 vessels were treated per one process, and the same experiments were repeated three times for calculating the average values of the data.

The results are shown in Table 3 as below.

TABLE 3

Forming percentage and produced amount of the garlic microbulbs, and the percentage of vitrification of plants in media, according to the light condition

| illumina-tion condition (lux) | Micro bulb forming percentage (number of formed bulbs/number of plants × 100) (%) | fresh weight of micro bulbs produced per bottle (g/Bottle) | vitrification percentage (nos. of vitri-fication cases/ plants × 100) (%) |
|---|---|---|---|
| 0 | 77.2 | 25.9 | 13.2 |
| 200 | 76.9 | 24.3 | 12.3 |
| 500 | 77.9 | 24.3 | 12.6 |
| 1,000 | 78.2 | 24.6 | 12.2 |
| 2,000 | 78.0 | 24.3 | 12.1 |
| 5,000 | 77.1 | 24.8 | 12.4 |
| 10,000 | 73.4 | 20.4 | 12.3 |

As seen from the result of experiment 2, the percentage of forming micro bulbs and the amount of the garlic microbulbs produced by this method was not reduced. In other words, once the suitable conditions of media and temperature are controlled, the storage-tissues of garlic may grow well without any restrictions under the dark condition.

In particular, a certain trend was observed in which the less the amount of light, the more the amount of the produced microbulbs. This seems to be resulted from poor of vegetative growth due to the inactive photosynthesis of the plant (garlic) body.

In fact, the groups treated with a highly intensity of radiation resulted in a phenomenon which the leaves of garlic were grown with green color. From these observation, a theory may be deduced in which the process for producing the microbulbs of garlic in vitro should be carried out in the culturing room under the dark-condition without any artificial illumination instead of the conventional condition.

Since the light doesn't have to be radiated from a constant direction according to the method of the present invention, there is no need to construct the culturing beds as used in the prior art, and/or the culturing containers may be arranged in the manner of increasing the utilizing-efficiency of space in the culturing room. Such culturing room may provide the workers with the various advantages including, for example, the reduced electric expense for lightening and air conditioning, and the efficient utilization of the space in the room.

Example 3
A Synergistic Efficiency Resulted from both the Liquid-Media/Dark Condition Culture The liquid-type media used in the experiment was prepared by adding not agar but 20~200 g/l of sucrose to the MS media. pH was adjusted to about 5.8 by using 1N NaOH and 1N HCl solutions. The media was divided by each volume of 80 ml and introduced into the round shape of polypropylene vessels (diameter of 110 mm×height of 45 mm) and autoclaved at 120° C. for 15 minutes. After cooling the media to the ambient temperature, 100 samples of plant bodies (garlic) were implanted per vessel. After developing the micro bulbs for 6 weeks in the culturing room, each determination of 1) microbulb-forming percentage, 2) the productivity of microbulb, and 3) causing the vitrification of plant body was carried out.

The condition of the culturing room was controlled for the temperature of 25±1° C., and with no artificial illumination besides the light from outside. 50 vessels were treated per one process, and the same experiments were repeated three times for calculating the average values of the data. The results are shown in Table 4 as below.

TABLE 4

Forming percentage and the produced amount of the garlic microbulbs, and the percentage of vitrification of plants in media, according to the dark condition with use of the liquid media

| Sucrose conc. (g/l) | Micro bulb forming percentage (number of formed bulbs/number of plants × 100) (%) | fresh weight of micro bulbs produced per bottle (g/Bottle) | vitrification percentage (nos. of vitri-fication cases/ plants × 100) (%) |
|---|---|---|---|
| 20 | 0.00 | 0 | 98.3 |
| 40 | 0.35 | 0.3 | 98.3 |
| 60 | 15.7 | 2.4 | 37.6 |
| 80 | 77.1 | 24.8 | 12.4 |
| 100 | 78.7 | 19.5 | 12.7 |
| 120 | 79.3 | 23.9 | 10.0 |
| 140 | 83.8 | 27.9 | 6.9 |
| 160 | 70.9 | 20.7 | 2.2 |
| 180 | 49.0 | 14.3 | 18.5 |
| 200 | 20.4 | 9.3 | 55.6 |

As seen from the result of experiment 3, the percentage of forming micro bulbs and the amount of the garlic microbulbs produced by the method under the dark condition with use of the liquid media exhibited the significant differences between the various groups having the different concentrations of sucrose. From the group having the sucrose concentration of 140 g/l in media, the highest forming percentages and the largest amount of the produced garlic microbulbs was obtained, and the percentage of vitrification of plants in media was also shown as being the lowest level.

Example 4

The media used in the experiment was prepared by verifying each concentrations of ammonium nitrate or potassium nitrate as being the levels of ⅛×, ¼×, ½×, 1× and 2× with respect to those of MS basal media. To each media, the amounts of 140 g/l sucrose were added.

The liquid type media was used as the culturing media, and the pH were respectively adjusted to about 5.8 by using 1N NaOH and 1N HCl solutions. The media was divided by each volume of 80 ml and introduced into the round shape of polypropylene vessels (diameter of 110 mm×height of 45 mm) and autoclaved at 120° C. for 15 minutes.

After cooling the media to the ambient temperature, 100 samples of in vitro garlic shoots were implanted per vessel. After developing the micro bulbs for 6 weeks in the culturing room, each determination of 1) microbulb-forming percentage, 2) the productivity of microbulb, and 3) causing the vitrification of plant body was carried out.

The condition of the culturing room was controlled for the temperature of 25±1° C., and with no artificial illumination. 50 vessels were treated per one process, and the same experiments were repeated three times for calculating the average values of the data. The results are shown in Table 5 as below.

TABLE 5

Forming percentage and the produced amount of the garlic microbulbs, and the percentage of vitrification of plants in media, under the dark condition/liquid media, according to the concentration of nitrogen source

| Nitrogen source | relative conc. (to MS basal media) | Micro bulb forming percentage (number of formed bulbs/number of plants × 100) (%) | fresh weight of micro bulbs produced per bottle (g/Bottle) | vitrification percentage (nos. of vitrification cases/plants × 100) (%) |
|---|---|---|---|---|
| ammonium nitrate | 1/8 | 75.4 | 23.1 | 3.4 |
|  | 1/4 | 88.5 | 30.1 | 3.2 |
|  | 1/2 | 85.1 | 28.2 | 5.3 |
|  | 2 | 65.5 | 20.4 | 12.4 |
| potassium nitrate | 1/8 | 66.5 | 13.5 | 8.4 |
|  | 1/4 | 75.4 | 20.6 | 7.2 |
|  | 1/2 | 84.1 | 27.5 | 7.1 |
|  | 1 | 83.8 | 27.9 | 6.9 |
|  | 2 | 83.4 | 27.6 | 6.7 |

The experimental results obtained from Example 4 was as shown in Table 5, in which the concentration of the nitrogen source in forms of ammonium nitrate or potassium nitrate was controlled to ⅛, ¼, ½, 1 and 2× of the MS basal media.

In case of treating the ammonium nitrate as nitrogen source, the productivity and the forming percentage of the microbulbs were increased when the concentration reduced to ½ or ¼ of the regular concentration. On the contrary, in case of using potassium nitrate, there were only a slight differences between the groups of ½, 1 and 2× concentrations relative to the regular one. Furthermore, below the concentration of ¼×, the worse results were obtained.

Therefore, in order to cause the microbulbs to be formed with using the liquid media and dark condition, it is preferable to alter the concentration of nitrogen source in the media. In particular, a ¼ diluted concentration is preferable in case using ammonium nitrate as nitrogen source in media, while the regular concentration is preferable in case of using potassium nitrate.

Example 5
Effect of Auxin (Naphthalene Acetic Acid; NAA)

The liquid media used in the experiment were prepared by adding 412.5 mg/l of ammonium nitrate and 475 mg/l of potassium nitrate with respect to those of MS media. To each media, the amounts of 140 g/l sucrose were added.

In order to determine the effects of NAA in the various concentrations, seven (7) kinds of the concentration levels were given to the liquid media, and the pH were respectively adjusted to about 5.8 by using 1N NaOH and 1N HCl solutions. The media was divided by each volume of 80 ml and introduced into the round shape of polypropylene vessels (diameter of 110 mm×height of 45 mm) and autoclaved at 120° C. for 15 minutes.

After cooling the media to the ambient temperature, 100 samples of plant bodies (garlic) were implanted per vessel. After developing the bulbs for 6 weeks in the culturing room, each determination of 1) microbulb-forming percentage, 2) the productivity of microbulb, and 3) causing the vitrification of plant body was carried out.

The condition of the culturing room was controlled for the temperature of 25±1° C., and with no artificial illumination. 50 vessels were treated per one process, and the same experiments were repeated three times for calculating the average values of the data. The results are shown in Table 6 as below.

TABLE 6

Forming percentage and the produced amount of the garlic microbulbs, and the percentage of vitrification of plants in media, under the dark condition/liquid media, according to the concentration of Auxin (NAA)

| conc. of NAA (mg/l) | Micro bulb forming percentage (number of formed bulbs/number of plants × 100) (%) | fresh weight of micro bulbs produced per bottle (g/Bottle) | vitrification percentage (nos. of vitrification cases/ plants × 100) (%) |
|---|---|---|---|
| 0 | 83.8 | 27.3 | 6.9 |
| 0.1 | 83.4 | 27.8 | 6.4 |
| 0.2 | 88.3 | 28.2 | 6.4 |
| 0.5 | 91.1 | 28.9 | 5.3 |
| 1.0 | 88.4 | 28.6 | 6.0 |
| 2.0 | 80.1 | 27.3 | 7.1 |
| 5.0 | 65.1 | 20.3 | 7.0 |

In general, it is known in the field of art that when added to the media, auxin can promote the formation of garlic microbulbs in vitro. The preferable concentrations of NAA in the media when used to promote the growth of garlic microbulbs are given in Table 6. There seems no significant differences in the results between the group having no auxin component and the groups treated with 0.1 to 5 mg/l of NAA. From these results, it is deduced that the formation of garlic microbulbs depends mainly on the nutrients and additives in the media and the environmental conditions, rather than on the plant growth regulators such as NAA. However, it is also believed that 0.5 mg/l concentration of NAA, if used, is preferable for promoting the growth of garlic under the predetermined condition, since the group treated with such concentration of NAA exhibited the best productivity. The expression level of the vitrification was not significantly different between the groups having the various concentrations of NAA, but the reduction of vitrification level was observed until the concentration reached 0.5 mg/l of NAA.

The liquid media can provide with the following advantages over the solid type media of the prior arts, which may result from using in the process according to the present invention:

1. The material costs for culturing process may be significantly saved by avoiding the use of expensive gelling agents, such as agar.

2. The work efficiency may be improved, since the liquid-type sterilized media according to the present invention does not solidified even in low temperature and can occasionally be used whenever required, over the long storage period. In contrast, the solid-type media should be processed by adding agar or phytagel as the gelling agent, dissolving and sterilizing the media at high temperature, dividing the media into each vessels in the liquid state, and using in the subsequent processes after solidified below 40° C.

3. The disposal treatment is easy after the processes are completed. The liquid type media may readily be treated as the same manner as the conventional treatment processes of the waste water, or re-used as the conventional fertilizer. However, an additional treatment processes should be carried out when the semi-solid type media according to the prior art is disposed, which is very complicated and difficult.

4. The plant can uptake the nutrients of the media with ease. In case of adding Agar to the media, it reduces the water potential in the media (Devergh et al 1981, 1982). Accordingly, the use by the plants may be restricted. Furthermore, Romberger and Tabor (1971) reported that the agar media itself inhibit the flow of the nutrients in the media, and therefore the harmful materials released from the plant body may be accumulated in a certain place. In ordinary cases using the liquid type media, since the respiration condition for the plants become worse, the shaking and/or air supplying into the media is essential. It is the additional advantages of the present invention that the aforementioned liquid type media may be used in the production of the garlic microbulbs in the stationary state without any air-supplying equipments.

Furthermore, in general, overall equipments in the culturing room consist of the air-conditioner for controlling the ambient temperature in the room, the light sources (generally installed above the beds) for providing with the illumination for the cultures, and so forth. In this regards, however, the application of the dark condition according to the present invention can provide with the additional advantages as follows:

1. The expenses for buying, installing and managing the equipments for illumination and/or air conditioning in the room can be avoided, therefore, the total cost for production can be further reduced.

2. Since there is no heat source in the room, the less cost is consumed for air conditioning (i.e. for temperature), such as, for example, the electric expense as well as the expenses for installing and managing the various equipments. In particular, relatively a long period is needed in production of the tissues of garlic microbulbs, the great effect may be expected.

3. The expenses for the electric power resulted from the lightening and/or air-conditioning of the room may be reduced preferably by 80% as before.

4. As aforementioned, the various equipments may be avoided by using the dark-condition and liquid type media in the present invention. Furthermore, the beds for supporting the culturing vessels may be arranged as the stacks. Accordingly, the efficiency for utilizing the space in the room may highly be increased.

According to the present invention, an improvement in the productivity of the method for production of garlic microbulbs may be achieved without exhibiting the vitrification phenomena of the plant tissue. Furthermore, in the resulting total costs for production of garlic microbulbs, a significant amount may also be saved by the above-mentioned advantages according to the present invention.

What is claimed is:

1. A method for producing microbulbs of Garlic in vitro by culturing tissues, comprising the steps of:
   a) isolating and excising virus-free tissues having a length of between 0.2 and 0.3 mm;
   b) inoculating the excised tissues from meristem tissue of Garlic onto a primary solid media containing 6.5 g/l of agar;
   c) culturing the tissues inoculated onto the primary solid media containing 6.5 g/l of agar under a cyclable sixteen hour light period and eight hour darkness period for four weeks;
   d) propagating plantlets regenerated from the cultured tissues at propagating media for four weeks;
   e) transferring the propagated plantlets to a liquid media, adding 90 g/l of sucrose and plant growth regulators to the liquid media, and culturing primarily;
   f) transferring the primarily cultured tissues to the liquid media having the same composition as the media used in step e, and adding 140 g/l of sucrose and plant growth regulators to the liquid media;
   g) secondarily culturing the tissues of step e in the room under 20 lux of illumination for six weeks; and
   h) harvesting the microbulbs from the virus-free garlic plants in vitro in which steps f and g are carried out in Murashige-Skoog liquid media having a reduced quantity of $NH_4NO_3$, and culturing under 20 lux of illumination.

2. The method according to claim 1, wherein the tissues used in step a are obtained from the meristem tissues of parent body of Garlic.

3. The method according to claim 1, wherein the primary solid media used in step b is Murashige-Skoog media that reduces the quantity of $NH_4NO_3$ by adding 0.2 mg/l of Cytokinin (BA), 20 g/l of sucrose and 6.5 g/l of agar.

4. The method according to claim 1, wherein the tissues used in step c are obtained from an axillary bud grown in vitro within two months.

5. The method according to claim 1, wherein the liquid media used in step e is prepared modified Murashige-Skoog media having a reduced quantity of $NH_4NO_3$ which is one-fourth that of Murashige-Skoog basal media (412.5 mg/l), and 90 g/l of sucrose.

6. The method according to claim 1, wherein the primary culturing step e is carried out within ten days.

7. The method according to claim 1, wherein the liquid media used in step e is prepared modified Murashige-Skoog media having a reduced quantity of $NH_4NO_3$ which is one-fourth that of Murashige-Skoog basal media (412.5 mg/l), and 140 g/l of sucrose.

8. The method according to claim 5, wherein 0.5 to 2.0 mg/l of Auxin (NAA) is used in the primary culturing steps as the plant growth regulator.

9. The method according to claim 7, wherein 0.5 to 2.0 mg/l of Auxin (NAA) is used in the liquid media as the plant growth regulator.

10. A method for producing microbulbs of Garlic in vitro by culturing tissues, comprising the steps of:
   a) isolating and excising virus-free tissues having a length of between 0.2 to 0.3 mm obtained from the meristem tissue of parent body of Garlic;
   b) inoculating the excised tissues from the meristem tissue of Garlic onto a primary solid media comprising inorganic salts of Murashige-Skoog media, 0.2 mg/l of Cytokinin (BA), 20 g/l of sucrose and 6.5 g/l of agar;
   c) transferring plantlets regenerated from the cultured tissues to a primary solid media comprising inorganic salts of Murashige-Skoog media, 2 mg/l of Cytokinin (BA), 20 g/l of sucrose and 6.5 g/l of agar, and culturing at 25° C. for four weeks;
   d) transferring the cultured tissues to a liquid media prepared modified of Murashige-Skoog media having a reduced quantity of $NH_4NO_3$ which is one-fourth that of Murashige-Skoog basal media (412.5 mg/l), adding 90 g/l of sucrose to the liquid media, and culturing for ten days;
   e) transferring the cultured tissues to a liquid media prepared modified Murashige-Skoog media having a reduced quantity of $NH_4NO_3$ which is one-fourth that of basal media (412.5 mg/l), adding 140 g/l of sucrose to the liquid media, and culturing under 20 lux of illumination for six weeks; and f) harvesting the microbulbs from the cultured plantlets in which the steps d and e are carried out in the liquid Murashige-Skoog media prepared by using 0.5 to 2.0 mg/l of Auxin (NAA) as a plant growth regulator, and culturing under 20 lux of illumination.

11. The method according to claim 6, wherein 0.5 to 2.0 mg/l of Auxin (NAA) is used in the primary culturing step as the plant growth regulator.

* * * * *